(12) United States Patent
Gerges et al.

(10) Patent No.: US 11,200,993 B2
(45) Date of Patent: Dec. 14, 2021

(54) RADIATION PROTECTION CLOTHING ARRANGEMENT AND METHOD OF WEARING SAME

(71) Applicants: Anton Gerges, Offenbach/Main (DE); Steve Gerges, Offenbach/Main (DE)

(72) Inventors: Anton Gerges, Offenbach/Main (DE); Steve Gerges, Offenbach/Main (DE)

( * ) Notice: Subject to any disclaimer, the term of this patent is extended or adjusted under 35 U.S.C. 154(b) by 351 days.

(21) Appl. No.: 16/366,109

(22) Filed: Mar. 27, 2019

(65) Prior Publication Data
US 2019/0304613 A1    Oct. 3, 2019

(30) Foreign Application Priority Data
Mar. 28, 2018 (EP) ..................................... 18164521

(51) Int. Cl.
*G21F 3/02*    (2006.01)
*A61B 6/10*    (2006.01)

(52) U.S. Cl.
CPC ............... *G21F 3/02* (2013.01); *A61B 6/107* (2013.01)

(58) Field of Classification Search
CPC .......... A47B 81/00; A61B 6/107; G21F 3/00; G21F 3/02; G21F 3/025
USPC ....... 2/255, 259, 260, 261, 264, 271, 81, 85, 2/93, 87, 216, 82, DIG. 5; 248/121, 158, 248/161
See application file for complete search history.

(56) References Cited

U.S. PATENT DOCUMENTS

| | | | | |
|---|---|---|---|---|
| 2,284,413 A | * | 5/1942 | Frentzel, Jr. .............. | E02F 3/64 210/533 |
| 3,052,799 A | | 9/1962 | Hollands et al. | |
| 3,846,708 A | * | 11/1974 | Franco ................ | H04L 27/1563 329/303 |
| 4,766,608 A | | 8/1988 | Cusick et al. | |
| 5,015,864 A | | 5/1991 | Maleki | |

(Continued)

FOREIGN PATENT DOCUMENTS

| CN | 103943163 A | 7/2014 |
|---|---|---|
| CN | 204654972 U | 9/2015 |

(Continued)

OTHER PUBLICATIONS

Extended European search report conducted in European Application No. 18 164 521.9 (dated Sep. 28, 2018) (with partial machine translation).

(Continued)

*Primary Examiner* — Gloria M Hale
(74) *Attorney, Agent, or Firm* — Greenblum & Bernstein, P.L.C.

(57) ABSTRACT

Radiation protection clothing arrangement and method of wearing the radiation protection clothing arrangement. The radiation protection clothing arrangement includes a flexible coat having radiation protection material configurable to surround, in a state of use, an interior space and a bottom edge, a weight-relieving device that is embodied as a support skeleton connected to the flexible coat and that absorbs a weight of the flexible coat in multiple locations distributed in a direction of gravity and a support device, to which the support skeleton is connected, being arranged within a space extending in the direction of gravity from the interior space and being supportable, in the state of use, on an underlying surface.

20 Claims, 10 Drawing Sheets

(56) References Cited

U.S. PATENT DOCUMENTS

| | | | |
|---|---|---|---|
| 5,115,140 A * | 5/1992 | Rodriguez | G21F 3/02 |
| | | | 174/388 |
| 5,220,175 A | 6/1993 | Cole | |
| 5,834,789 A | 11/1998 | Marchione | |
| 8,558,204 B2 | 10/2013 | Rees | |
| 8,674,330 B2 | 3/2014 | Beck | |
| 8,777,168 B2 | 7/2014 | Hassid | |
| 8,925,553 B2 | 1/2015 | Byers et al. | |
| 2009/0256044 A1 | 10/2009 | Miller et al. | |
| 2012/0228439 A1 | 9/2012 | Hassid | |
| 2018/0075936 A1* | 3/2018 | Milstein | G21F 3/025 |
| 2019/0043628 A1* | 2/2019 | Milstein | G21F 3/02 |
| 2019/0304613 A1* | 10/2019 | Gerges | A61B 6/107 |

FOREIGN PATENT DOCUMENTS

| | | |
|---|---|---|
| CN | 205645288 U | 10/2016 |
| EP | 1 052 651 B1 | 3/2000 |
| JP | 2013-13499 | 1/2013 |
| KR | 101880620 B1 | 7/2018 |

OTHER PUBLICATIONS

English translation of Korea Office Action conducted in counterpart Korea Appln. No. 10-2019-0036033 (dated Apr. 23, 2020).

* cited by examiner

FIG. 1A
FIG. 1B
FIG. 1C
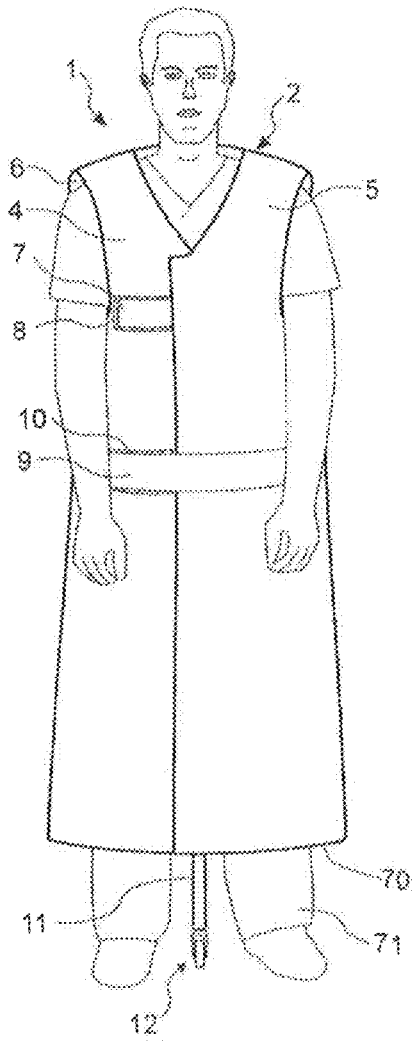
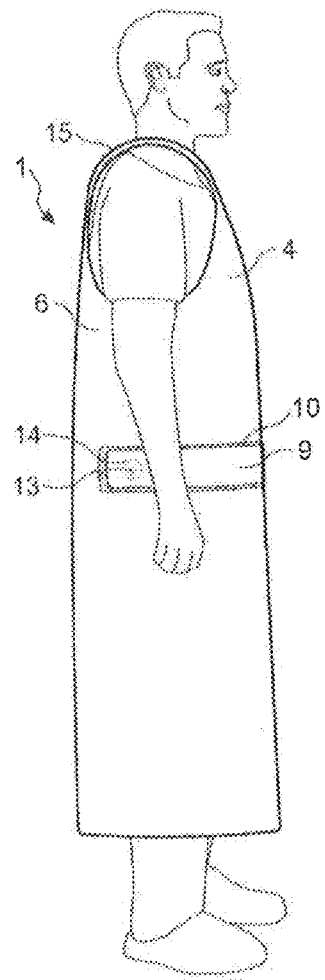
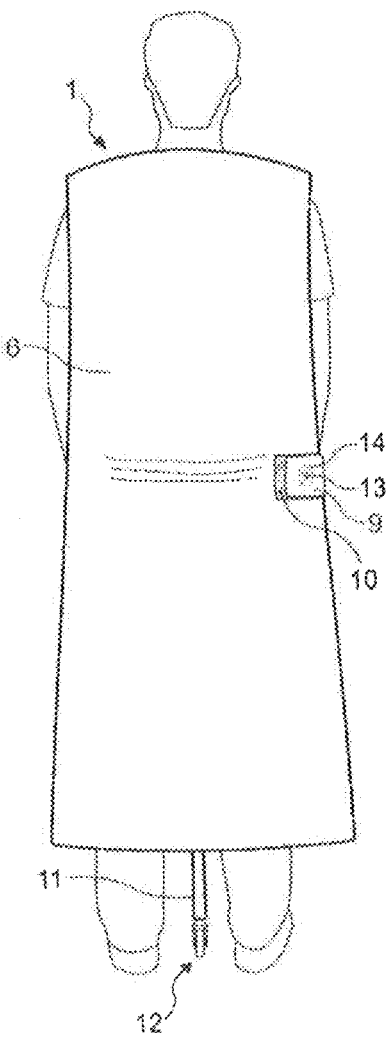

FIG. 2A  FIG. 2B  FIG. 2C
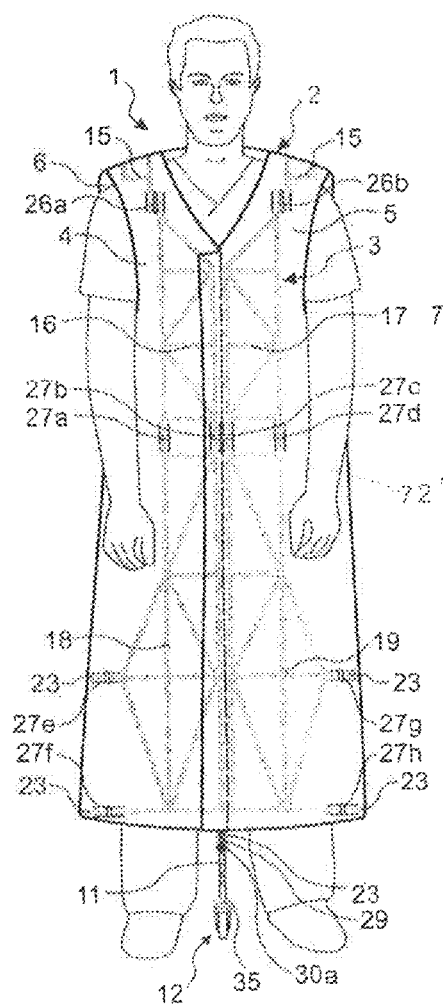
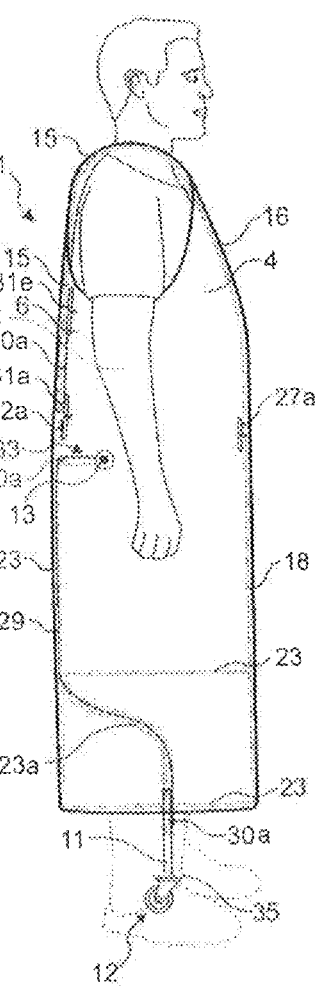
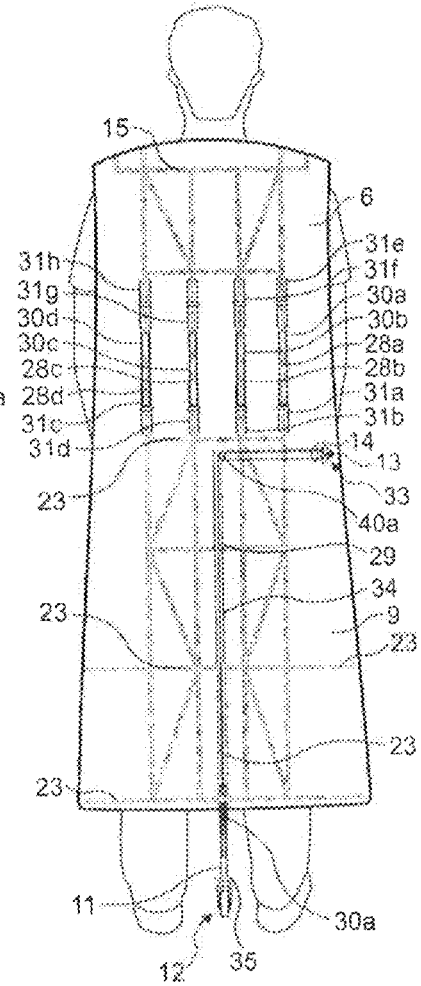
FIG. 2D  FIG. 2E
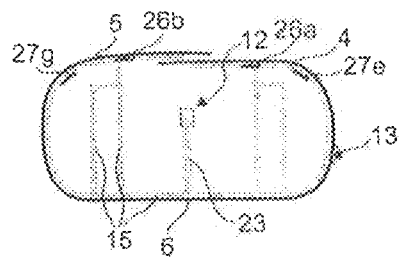
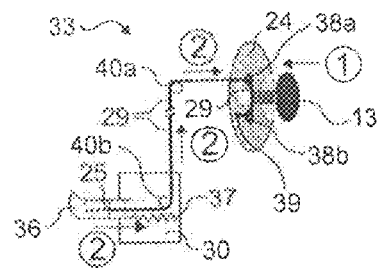

FIG. 3
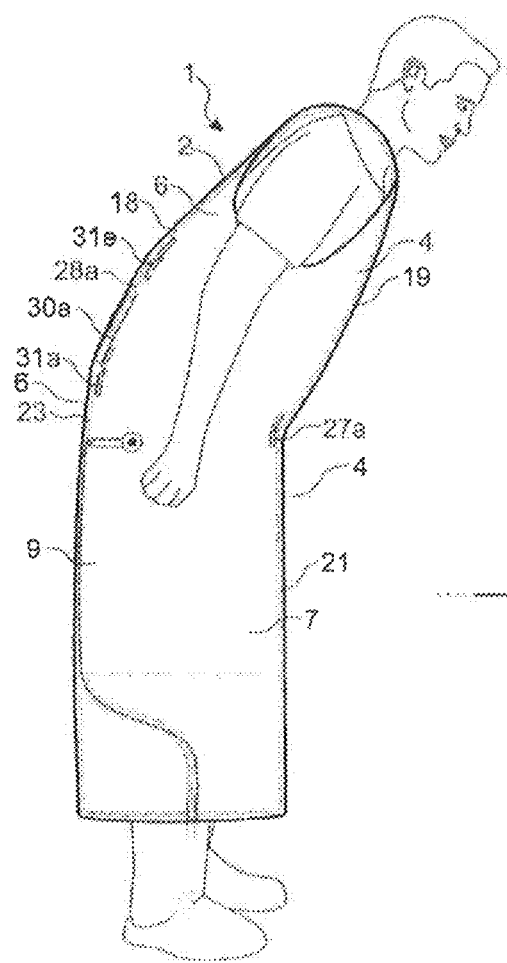
FIG. 11
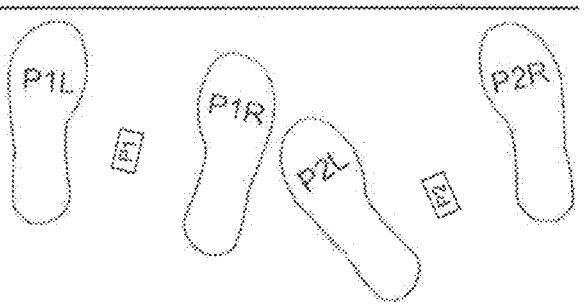
FIG. 12    FIG. 13
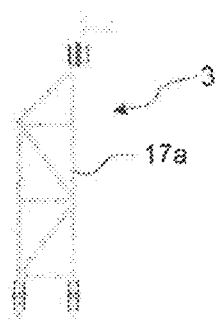
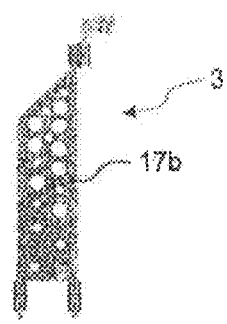

FIG. 4A
FIG. 4B
FIG. 4C
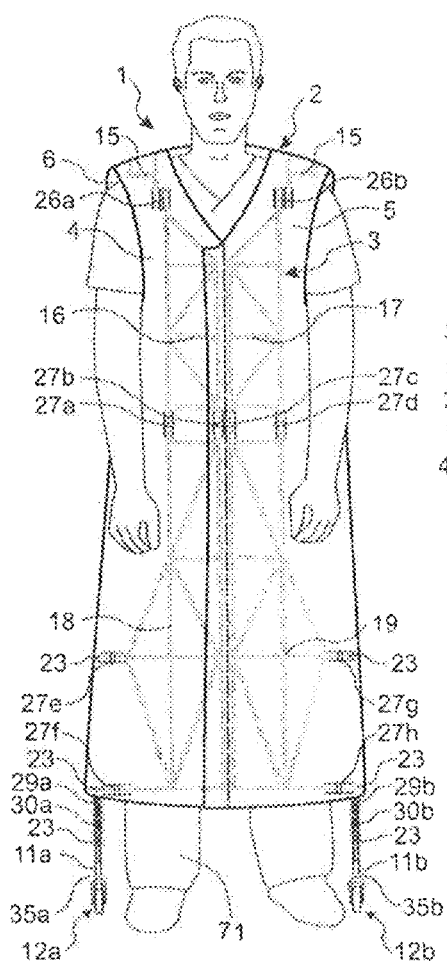
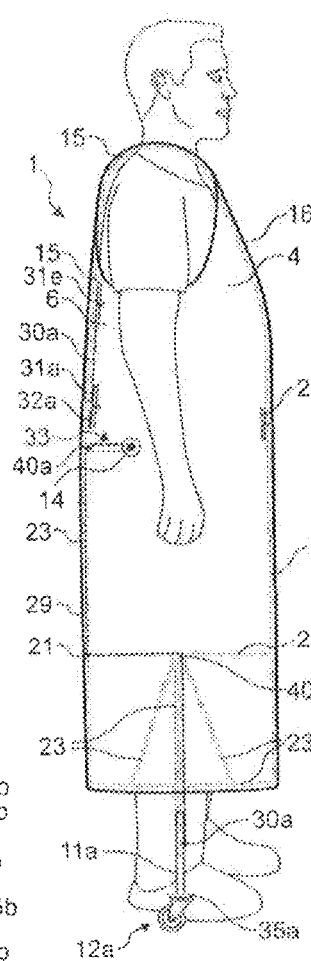
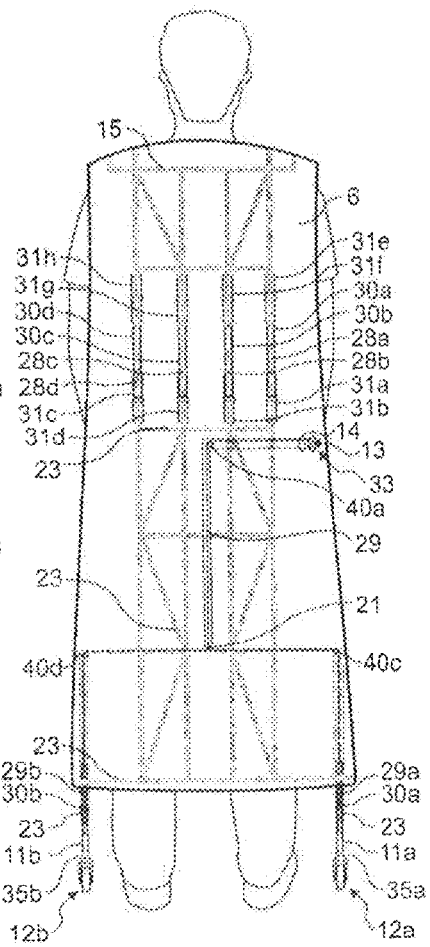
FIG. 4D
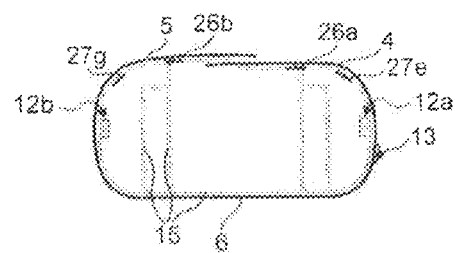

FIG. 7A  FIG. 7B  FIG. 7C
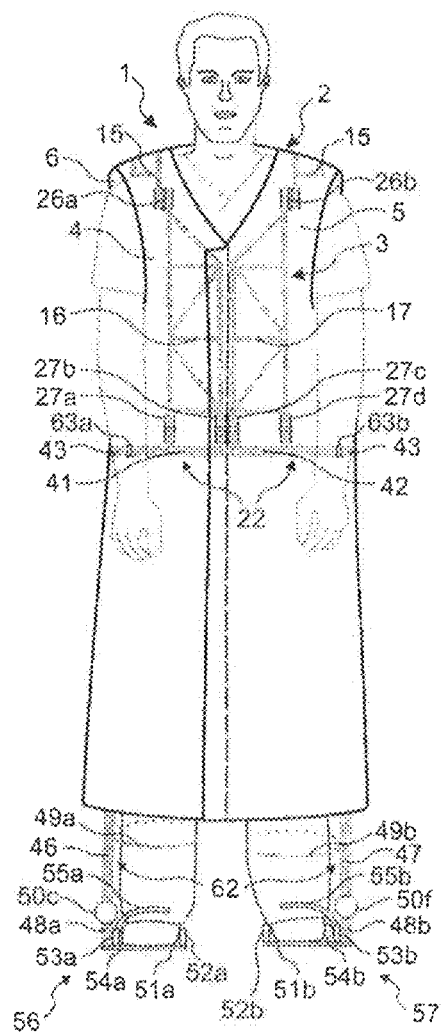
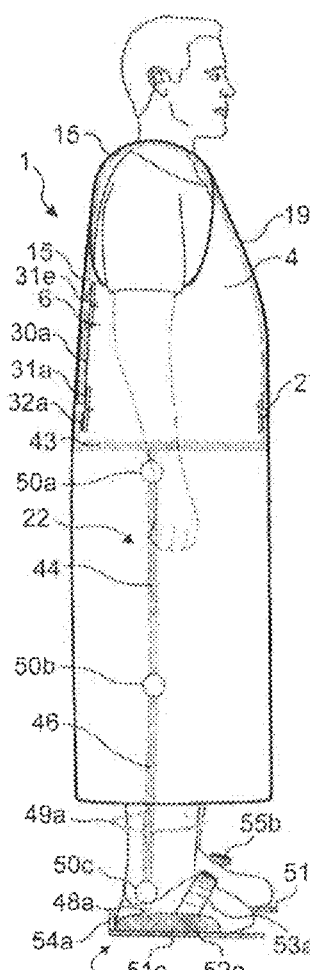
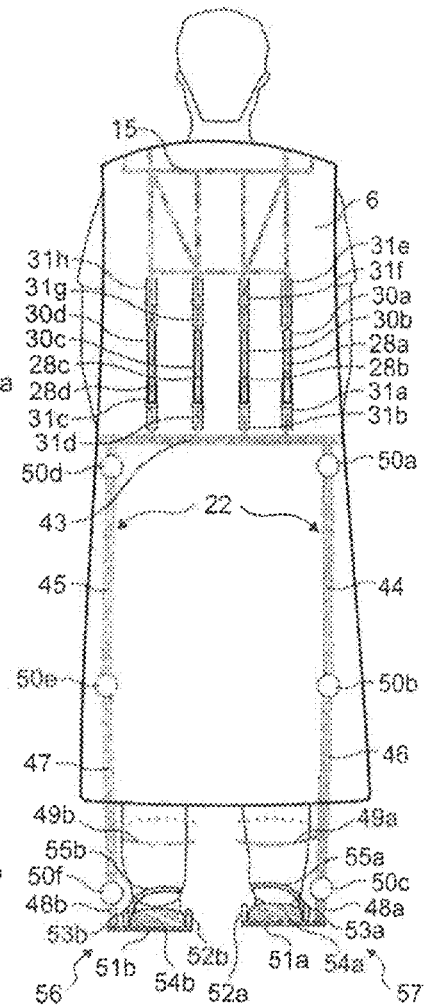
FIG. 7D  FIG. 7E
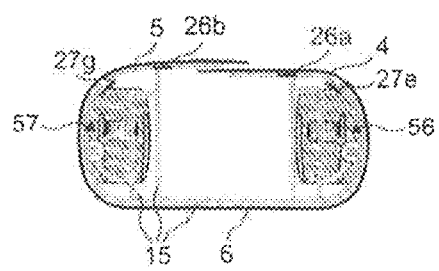
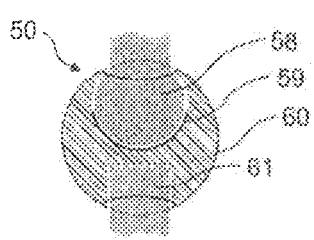

FIG. 10A
FIG. 10B
FIG. 10C
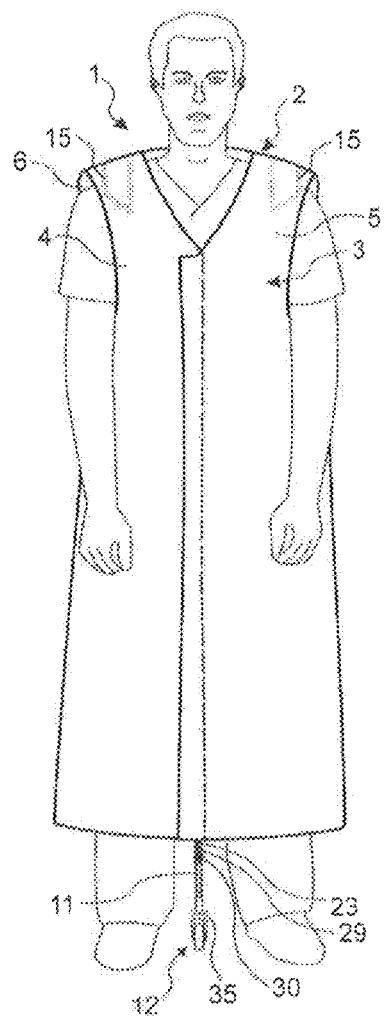
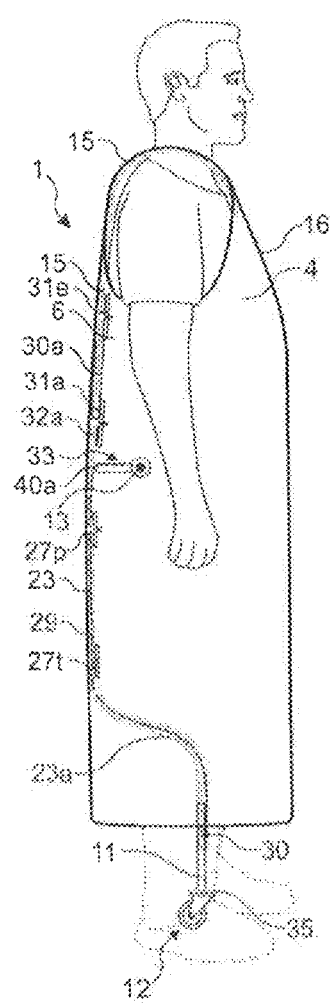
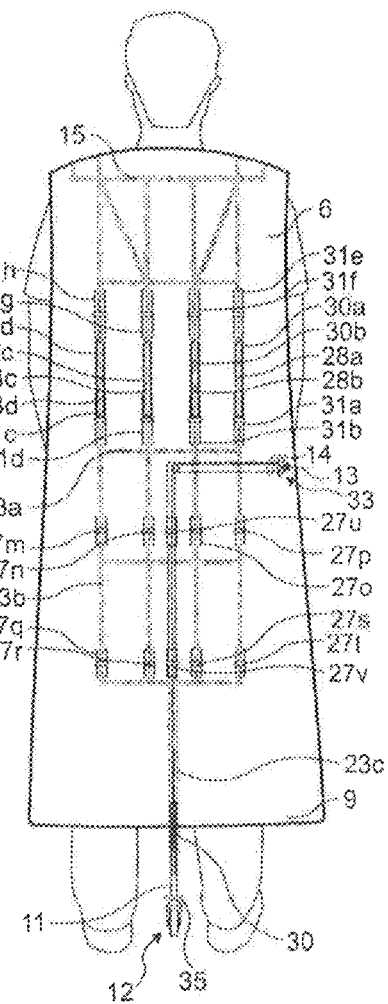
FIG. 10D
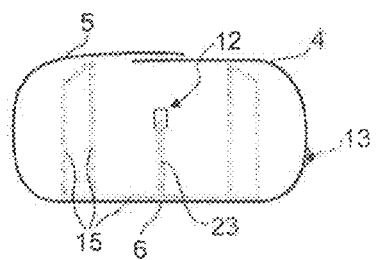

RADIATION PROTECTION CLOTHING ARRANGEMENT AND METHOD OF WEARING SAME

CROSS-REFERENCE TO RELATED APPLICATIONS

The present application claims priority under 35 U.S.C. § 119 of European Patent Application No. 18 164 521.9 filed Mar. 28, 2018, the disclosure of which is expressly incorporated by reference herein in its entirety.

BACKGROUND

1. Field of the Invention

The embodiments relate to a radiation protection clothing arrangement having a flexible coat which comprises radiation protection material and, in a state of use, encloses an interior space with a bottom edge, and having a weight-relieving device.

2. Discussion of Background Information

For diagnostic, therapeutic or surgical measures that are to be performed with exposure to radiation, physicians and other medical personnel depend on the wearing of special radiation protection clothing, for example, in the form of X-ray protection clothing. The X-ray protection clothing prevents X-rays from negatively affecting the human body of the medical personnel in an adverse manner. Protection against radioactive radiation is also necessary in nuclear environments. In order to produce a satisfactory protective effect, the radiation protection material must be provided with a certain thickness, which leads to a correspondingly high mass of the coat. A mass of 5 to 10 kg or more is normal in this case. When a person wears a coat of this type, it results in considerable physical strain. This high weight load can lead to fatigue symptoms, back pain, postural deformities, and muscular tension. The ability to concentrate during procedures on the patient can suffer. A persistent overstraining of the body can lead to damage over the long term, for example to spinal joints, vertebral bodies, and intervertebral discs.

Measures have therefore already been proposed for combining an adequate protection against rays with greater wearing comfort and lower strain. For example, European Patent No. EP 1 052 651 B1 shows the possibility not only of having the weight of the coat be borne by the shoulders of the person being protected, but of providing additional support points, for example on the hips in the person's back region. A similar design is also known from U.S. Pat. No. 3,052,799 A, or from U.S. Pat. No. 5,834,789 A. In this case, the entire weight of the coat is to be absorbed by the hips of the person being protected. A similar design is also known from U.S. Pat. No. 4,766,608 A.

In such a design of the radiation protection clothing arrangement, however, the person being protected still bears the entire weight of the coat, so that the weight load is merely transferred from the back to other body parts, for example, to the knees.

Another possibility for the protection against X-rays is described in U.S. Pat. Nos. 5,220,175 A, 5,015,864 A, or 8,925,553 B2. Here, X-ray protection shields are shown, behind which the person being protected can be positioned. However, an X-ray protection shield of this type is an obstacle around which the person being protected must reach when he/she wishes to perform actions on a patient. In addition, protection shields of this type require a relatively large amount of space, that is, a relatively large footprint on the floor, in order to prevent tipping, which causes difficulties when multiple persons being protected need to collectively perform operations on a patient. However, a situation such as this often occurs during surgical procedures, where a foot-to-foot situation is necessary for the ability to work together.

Another possibility for protection is to provide a rail arrangement or a crane arrangement on a ceiling of the room, which arrangement carries the coat. Such a possibility is shown in U.S. Pat. No. 8,558,204 B2 or U.S. Patent Publication No. 2009/0256044 A1. The rail arrangement or crane arrangement can fully accommodate the weight of the coat, but it limits the movement options of the person being protected, since said person can only move within the range of the rail arrangement or crane arrangement. Particularly where a room change is required, an X-ray protection arrangement of this type can only be used with increased effort.

A radiation protection clothing arrangement of the type named at the outset is known from U.S. Pat. No. 8,674,330 B2, for example. In this case, the coat is suspended on a frame that is supported on the floor by four casters. The four casters must form a relatively large footprint in order to prevent tipping.

A similar design is also known from U.S. Pat. No. 8,777,168 B2. Here, the coat is suspended in its shoulder region on a stand.

In both cases, a relatively large area and space requirement results, so that a radiation protection clothing arrangement of this type cannot be used in an operating room, where multiple persons being protected must stand in a relatively close adjacent position to one another, for example, in the aforementioned foot-to-foot situation. Furthermore, a radiation protection clothing arrangement of this type in many cases limits the movement options of the person being protected.

SUMMARY

Embodiments of the invention combine a highest possible radiation protection with a low mechanical load on the person being protected.

In embodiments, a radiation protection clothing arrangement of the type named at the outset includes a weight-relieving device embodied as a support skeleton that is connected to the coat and absorbs the weight of the coat in multiple locations distributed in the direction of gravity. The support skeleton is connected to a support device that can be set up on an underlying surface in a state of use and the support device is arranged within an extension of the interior space in the direction of gravity.

In a radiation protection clothing arrangement of this type, the weight of the coat can be diverted via the support device virtually entirely onto the floor or another underlying surface on which the person being protected is standing, for example, a platform at an operating table. The support device thus does not protrude outwardly past the coat, and therefore does not impede multiple persons being protected from standing closely together. The risk of the support device bumping against another object, for example an operating table or the like, when the person being protected moves is also low. The coat is also no longer suspended on the support skeleton solely in the shoulder region, but rather has multiple attachment points that are distributed in the direction of gravity. These points reduce the tipping risk of the radiation protection clothing arrangement. Thus, the person being protected can be virtually entirely relieved of the weight of the coat, and only needs to exert minimal strength to brace a coat standing essentially vertically in the direction of gravity against tipping forces that, as explained above, are small due to the distributed attachment of the coat to the support skeleton.

The embodiments described below on the basis of an X-ray protection clothing arrangement. Here, X-rays constitute a particular subtype of rays in general. Accordingly, the invention can also generally be used with other rays that can be hazardous to humans.

Preferably, the support skeleton is embodied to be movable. Because the support skeleton is not rigid, but rather movable and therefore flexible, it can follow movements of the person being protected together with the coat. The coat and the support skeleton can also be arranged relatively tightly around the body of the person being protected, so that the space required for the radiation protection clothing arrangement remains small and multiple persons being protected can work together in close spatial proximity. The support skeleton can preferably also adapt to the body of the person being protected, that is, the interior space surrounded by the support skeleton can preferably be modified. The support skeleton can enclose a larger interior space for a bulkier person and a smaller interior space for a thinner person. If the support skeleton is embodied to be movable, that is, deformable, it is not absolutely necessary that the support device be arranged within an extension of the interior space in the direction of gravity. With the movability of the support skeleton, the range of motion of a person who is protected by the radiation protection clothing arrangement is somewhat extended, so that it can also be permitted to a certain extent that the support device is located slightly outside the extension of the interior space in the direction of gravity.

Preferably, the support device comprises at least one caster. The support device can thus be moved across the floor or another underlying surface in a low-friction manner, so that the person being protected does not need to overcome any major resistance when he/she moves across the floor together with the radiation protection clothing arrangement. Two, three, four, or more casters can also be used instead of a single caster. These casters are then preferably all arranged within the extension of the interior space in the direction of gravity.

In alternative embodiments, the support device includes a foot attachment and/or leg attachment. The person being protected can connect his/her feet or his/her lower legs to the foot attachment. If the person being protected then moves his/her feet, the support device is also moved. However, the support device also diverts the weight of the coat onto the floor or another underlying surface.

In preferred embodiments, the coat and/or the support skeleton has a balanced mass distribution around the support device. Thus, in a vertical alignment, the radiation protection clothing arrangement is in a state of balance, that is, there is virtually no or only very little tilting moment that can be exclusively attributed to an uneven mass distribution. A slight tilting moment can result from the person being protected changing his/her body posture, for example, leaning the upper body forward. The accompanying loads on the body of the person being protected are relatively small, however, and can easily be absorbed. In any event, they are considerably smaller than the load caused by the weight of the coat.

Preferably, the support device is arranged outside of leg travel spaces that extend out of the interior space past the bottom edge. The leg travel spaces are the spaces in which the person being protected typically moves his/her legs. The leg travel spaces are thereby arranged slightly off-center to the left and right of a center plane through the radiation protection clothing arrangement. If the support device is arranged outside of the leg travel spaces, then it does not impede the movement of the legs of the person being protected. For example, the support device can be arranged on the aforementioned center plane when only one caster is provided, for example. The support device can also be connected, through a longer vertical segment in the back region of the coat, to the support skeleton, and can be curved in an S shape solely in a lower region in the direction of gravity, so that a person with knock knees is also not impeded by the support device.

The support device is preferably height-adjustable. The radiation protection clothing arrangement can thus be adapted to different body sizes of persons being protected. The height-adjustability of the support device can also be utilized for a different purpose. The person being protected puts on the radiation protection clothing arrangement without the support device resting on the underlying surface. For a relatively brief span of time, the entire weight of the radiation protection clothing arrangement then bears down on the shoulders of the person being protected. The person being protected can then stand on his/her tiptoes or can lift his/her shoulders by a sufficient amount in another manner. The height of the support device can then be adjusted such that the support device rests on the floor. If the person being protected then once again resumes a normal posture in which his/her feet are standing on the floor, a small distance results between a shoulder region of the coat and the shoulders of the person being protected, so that the person being protected no longer needs to support the weight of the radiation protection arrangement.

Preferably, the support skeleton is at least partially covered with a textile material. This has several advantages. On the one hand, an appealing outer design can be achieved. On the other hand, the haptics can be improved. Especially if the support skeleton is arranged internally in the coat, direct contact of the support skeleton with the person is avoided if a layer of the textile material is provided between the body of the person being protected and the support skeleton.

Preferably, the support skeleton is integrated into the coat. The support skeleton is thus not noticeable from the outside. In addition, it has a stabilizing function for the coat during storage. The risk of the coat becoming creased, and the radiation protection material thus becoming damaged, is reduced.

Preferably, at least some elements of the support skeleton are embodied to be length-variable and/or deformable. The deformable embodiment of elements of the support skeleton can be utilized for the movable connection of elements. It can also be provided as an additional feature, however. A length-variable embodiment of elements of the support skeleton is advantageous in the back region, for example, in order to allow the person being protected to bend his/her upper body.

In this case, it is preferred that the coat includes an excess length in the region of at least one of the length-variable and/or deformable elements. As long as the corresponding element has its shortest extension, the coat can have a "fold" here. If the person being protected then leans forward and arches his/her back accordingly, then the coat can be stretched so that the radiation protection function of the coat is maintained and no gaps occur.

Preferably, the support skeleton is formed from metal and/or plastic. In both cases, if appropriate materials are selected, a low-mass support skeleton can be formed that nevertheless exhibits relatively high mechanical stability.

Preferably, the support skeleton comprises a framework structure and/or a perforated plate arrangement. Both are possibilities for minimizing the mass of the support skeleton without sacrificing adequate stability.

Preferably, the support skeleton has a local load-bearing capacity that increases downwards in the direction of gravity. This accounts for the fact that a lower region of the support skeleton in the direction of gravity must absorb more weight overall than an upper region in the direction of gravity. In this manner, the design of the support skeleton can be "slimmed down" towards the top. This is beneficial because the person being protected typically acts with his/her hands and arms, which are also arranged in the upper region of the radiation protection clothing arrangement in the direction of gravity, and which are then impeded minimally, or even not at all, by the support skeleton.

In advantageous embodiments, at least one movable connection between elements of the support skeleton comprises at least one reset. The reset can, for example, be formed by a spring or a gas pressure cylinder. If the reset is provided in the back region of the coat or of the support skeleton, for example, they make it easier for the person being protected to straighten up from a hunched position.

In another aspect, embodiments are directed to radiation protection clothing arrangement having a flexible coat which include radiation protection material and which, in a state of use, surrounds an interior space with a bottom edge, and having a weight-relieving device in which the weight-relieving device is embodied as a self-supporting flexible support skeleton that is connected to the coat and absorbs the weight of the coat in multiple locations distributed in the direction of gravity. The support skeleton is connected to a support device which can be set up on an underlying surface in a state of use.

Embodiments are directed to a radiation protection clothing arrangement that includes a flexible coat having radiation protection material configurable to surround, in a state of use, an interior space and a bottom edge, a weight-relieving device that is embodied as a support skeleton connected to the flexible coat and that absorbs a weight of the flexible coat in multiple locations distributed in a direction of gravity, and a support device, to which the support skeleton is connected, being arranged within a space extending in the direction of gravity from the interior space and being supportable, in the state of use, on an underlying surface.

According to embodiments, the support skeleton may be embodied to be movable.

In accordance with other embodiments, the support device can include at least one caster.

In other embodiments, the support device may include at least one of a foot attachment or a leg attachment.

According to still other embodiments, at least one of the coat or the support skeleton may have a balanced mass distribution around the support device.

In other embodiments, the support device may be arranged outside of leg travel spaces that extend out of the interior space past the bottom edge.

Other embodiments can include that the support device is height-adjustable.

In accordance with embodiments, the support skeleton may be at least partially covered with a textile material.

In other embodiments, the support skeleton may be integrated into the coat.

In accordance with still other embodiments, at least some elements of the support skeleton may be embodied to be at least one of length-variable or deformable. The coat can include an excess length in a region of at least one of the length-variable or deformable elements.

According to other embodiments, the support skeleton can be formed from at least one of metal or plastic.

In still other embodiments, the support skeleton may include at least one of a framework structure or a perforated plate arrangement.

According to embodiments, the support skeleton can have a local load-bearing capacity that increases downwards in the direction of gravity.

In accordance with embodiments, at least one movable connection between elements of the support skeleton may include at least one reset.

Moreover, in embodiments, the support device may be arranged entirely within the space extending from the interior space in the direction of gravity.

In still other embodiments, the support device may be arranged to extend, in the direction of gravity, from the interior space into a space extending, in the direction of gravity, below the bottom edge.

Embodiments are directed to a method of wearing the above-described radiation protection clothing arrangement. The method includes placing a part of the support skeleton over a wearer's shoulders; closing the flexible coat to surround at least the wearer's torso to define the interior space; and adjusting a length of the support device so that the support device is supported on the underlying surface, to which the support skeleton is connected. After adjusting the length of the support device, the wearer's shoulders do not bear a weight of the support skeleton.

According to embodiments, while adjusting the length of the support device, the support device remains within the space extending from the interior space in the direction of gravity.

In accordance with still yet other embodiments, the support device may include an actuation device that is configured to release the support device from a locked position and to lock the support device in a support position.

Other exemplary embodiments and advantages of the present invention may be ascertained by reviewing the present disclosure and the accompanying drawing.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein:

FIGS. 1A-1C shows a first embodiment of a radiation protection clothing arrangement on a person being protected;

FIGS. 2A-2E shows the radiation protection clothing arrangement according to FIG. 1 with a transparently depicted coat;

FIG. 3 shows the radiation protection clothing arrangement according to FIG. 2 on a person in a hunched posture;

FIGS. 4A-4D shows a second embodiment of the radiation protection clothing arrangement;

FIGS. 7A-7E shows a fifth embodiment of the radiation protection clothing arrangement;

FIGS. 10A-10D shows a simplified embodiment of the radiation protection clothing arrangement;

FIG. 11 shows a schematic representation to illustrate a foot-to-foot situation at an operating table;

FIG. 12 shows a schematic representation of a section of a support skeleton in a framework embodiment; and FIG. 13 shows a schematic representation of a section of a support skeleton in perforated plate embodiment.

Identical and correlating elements are provided with the same reference numerals in all Figures.

Figure 5A:
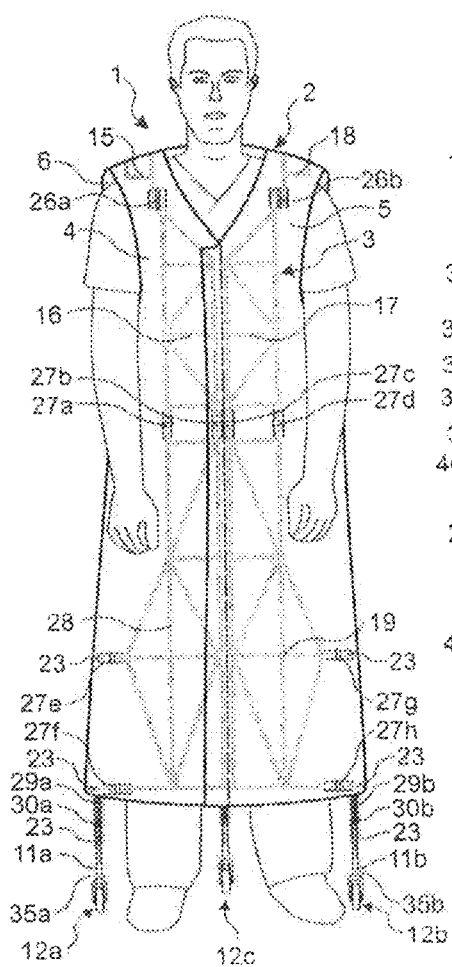
FIGS. 5A-5D shows a third embodiment of the radiation protection clothing arrangement.
Figure 5B:
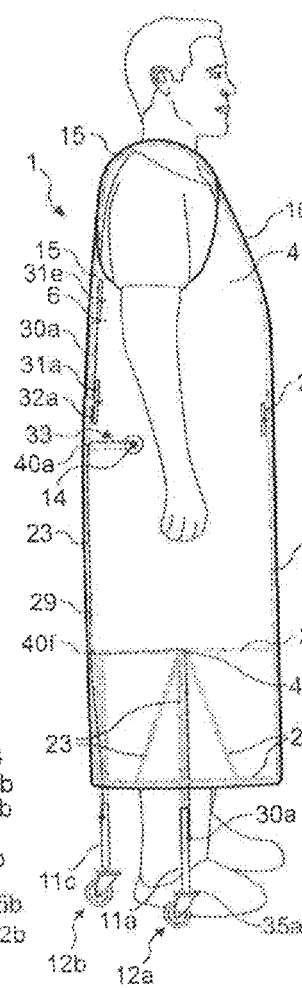
Figure 5C:
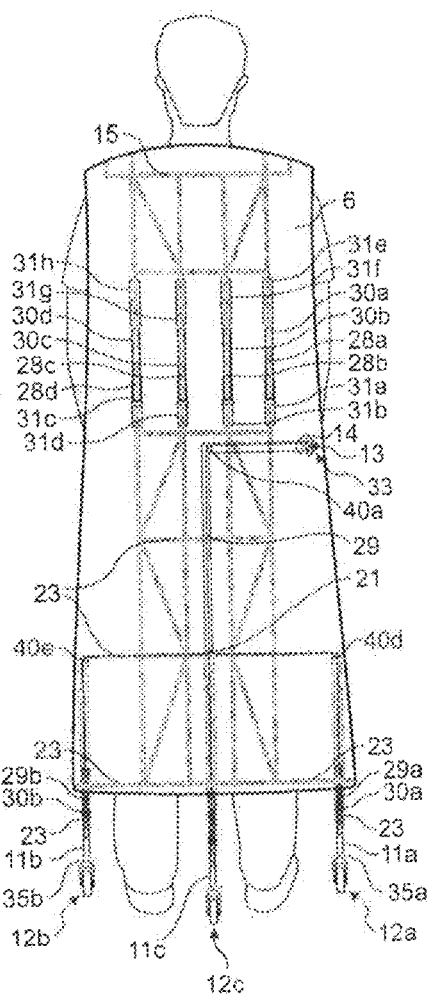
Figure 5D:
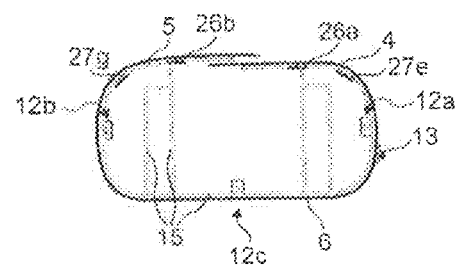
Figure 6A:
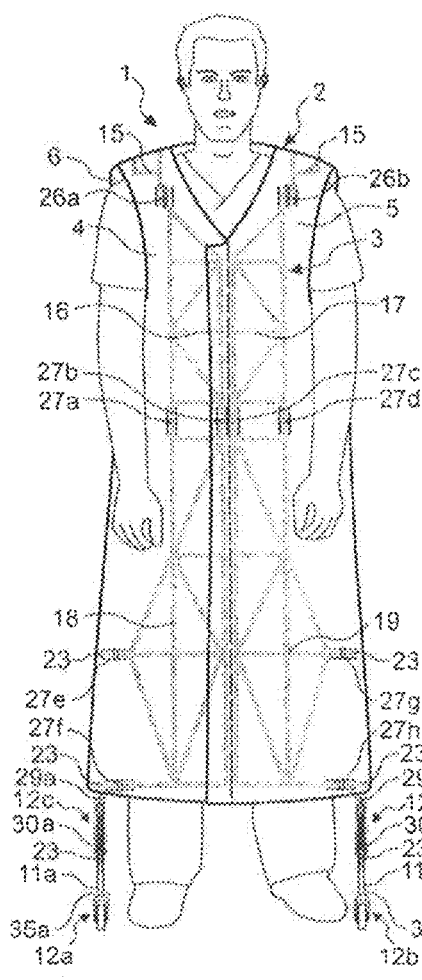
FIGS. 6A-6D shows a fourth embodiment of the radiation protection clothing arrangement.
Figure 6B:
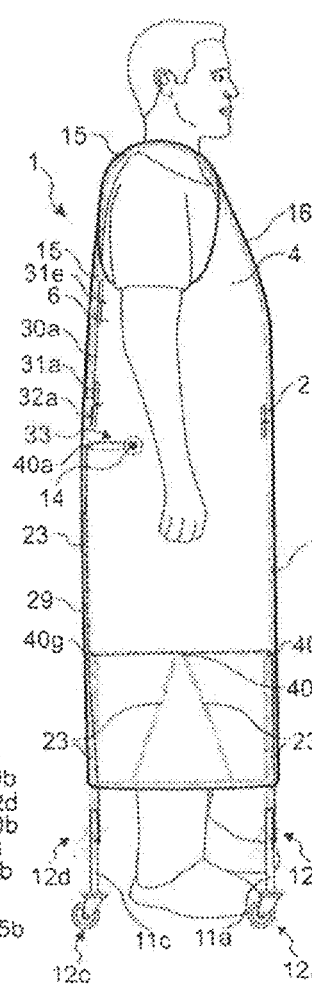
Figure 6C:
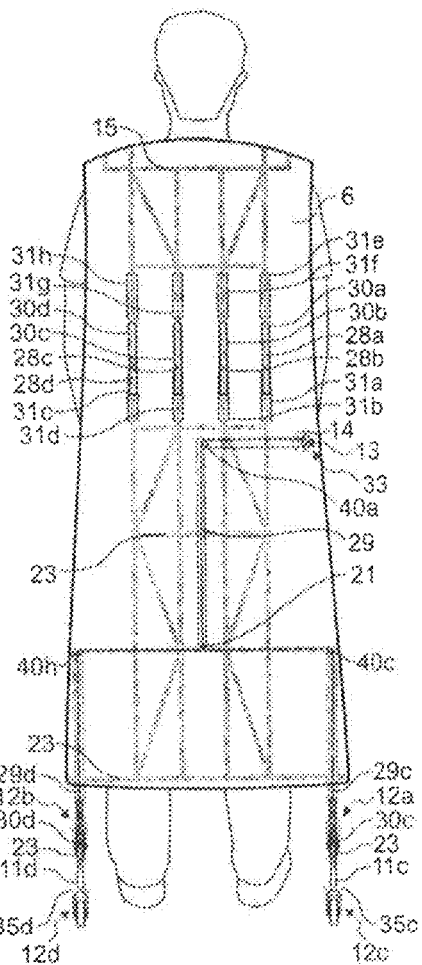
Figure 6D:
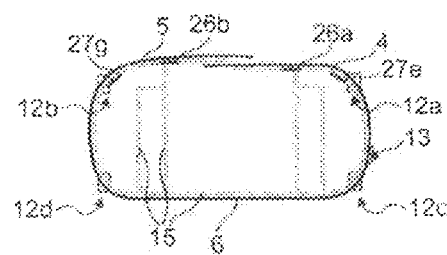
Figure 8A:
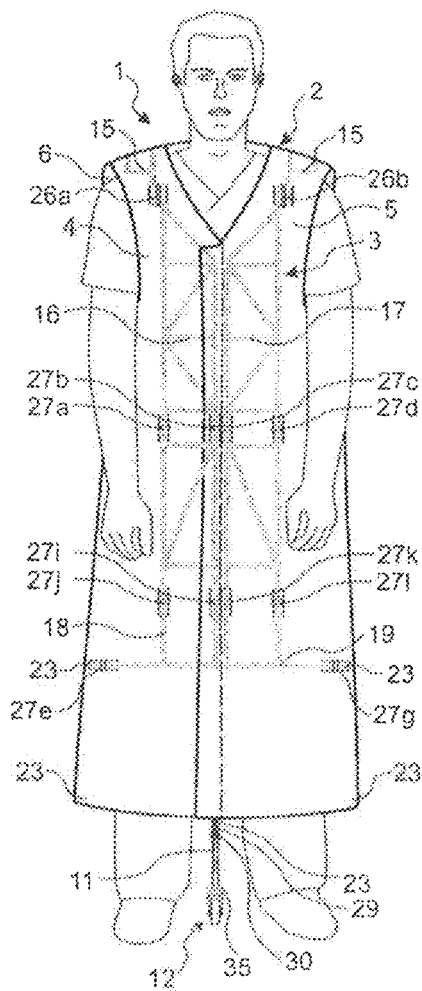
FIGS. 8A-8D shows a sixth embodiment of the radiation protection clothing arrangement.
Figure 8B:
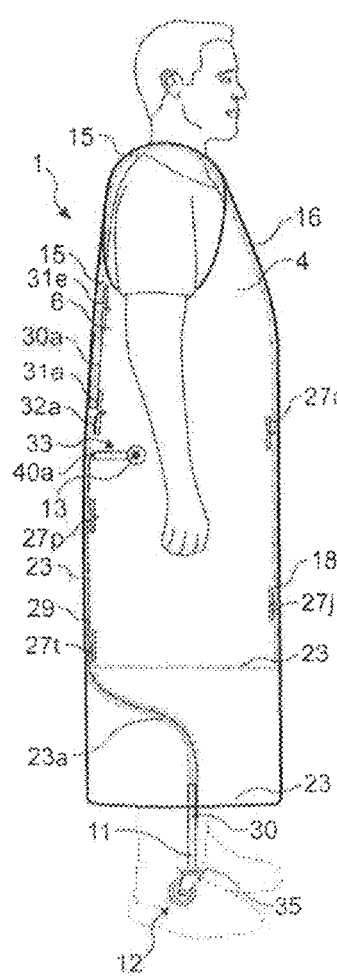
Figure 8C:
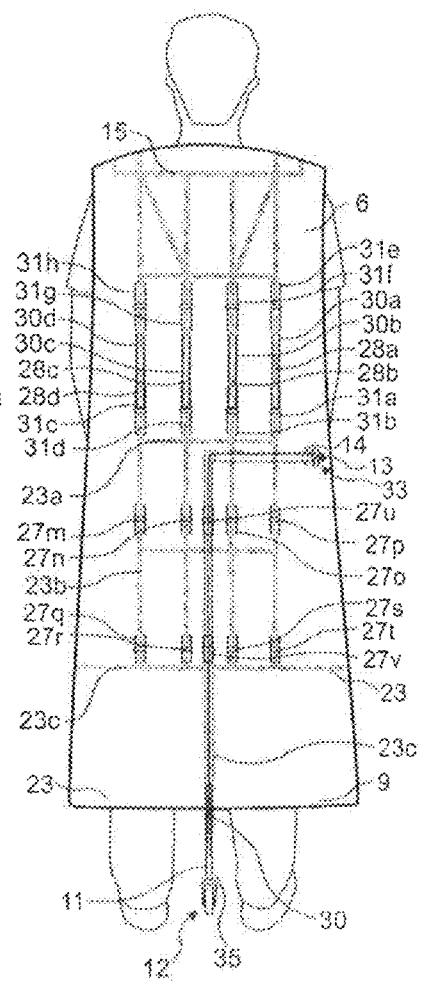
Figure 8D:
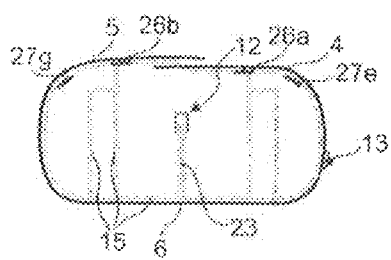

In all Figures, Subfigure "A" shows a front view, Subfigure "B" shows a side view, Subfigure "C" shows a rear view, and Subfigure "D" shows a top-down view.

DETAILED DESCRIPTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice.

The invention is described below on the basis of an X-ray protection clothing arrangement. However, it is equally usable with other rays, for example, in the field of nuclear energy. The type of protection depends on the materials used. Therefore, the term "X-ray protection clothing arrangement" can easily be replaced by "radiation protection clothing arrangement."

FIGS. 1A-1C and 2A-2E schematically show a radiation protection clothing arrangement in the form of an X-ray protection clothing arrangement 1 having a flexible coat 2, which comprises radiation protection material, and a support skeleton 3 that is not visible in FIGS. 1A-1C, but rather is only visible in FIGS. 2A-2C. In the present case, the coat 2 is arranged externally on the support skeleton 3, so that the coat 2 covers the support skeleton 3. The support skeleton 3 can also be integrated into the coat 2. On the inside, the support skeleton 3 can be covered with a padded textile material to allow the X-ray protection clothing arrangement 1 to be worn comfortably.

The X-ray protection clothing arrangement 1 is illustrated on a person being protected, which person has a body. The body is located in an interior space of the coat 2. The coat 2 and the support skeleton 3 are thereby flexible enough that the interior space has a variable size and can adapt to different sizes of the person being protected. The coat 2 comprises a bottom edge 70, out of which the legs 71 of the person being protected protrude.

At its lower end in the direction of gravity, the support skeleton 3 is connected to a support device 11, which in turn is provided at its lower end with a caster 12, which is preferably embodied as a swivel caster. The support device 11 is thus capable of diverting the entire weight of the X-ray protection clothing arrangement with the coat 2 and support skeleton 3 onto the floor or another underlying surface on which the legs 71 of the person being protected are standing.

As can be seen in FIGS. 2A-2E, the support skeleton 3 comprises a framework structure 16, 17. FIG. 12 schematically shows a section of the framework structure 17a. As an alternative thereto, FIG. 13 shows a perforated plate arrangement 17b that can be used instead of the framework structure 17a.

The support skeleton 3 is connected to the coat 2, namely in multiple locations, so that the support skeleton 3 can absorb the weight of the coat 2 in these multiple locations distributed in the direction of gravity. The support skeleton 3 thereby has a local load-bearing capacity that increases downwards in the direction of gravity, which will be explained further below. This accounts for the fact that, in its upper region in the direction of gravity, the support skeleton must support a lower mass of the coat 2 than in its lower region in the direction of gravity. This means that in its upper region in the direction of gravity, that is, in the region of the arms 72 of the person being protected, the support skeleton 3 can be embodied in a less substantial manner, and thus does not impede moving arms 72.

The coat 2 comprises a right side panel 4, a left side panel 5, and a rear section 6. In a ready-to-use or closed state of the coat 2, the left side panel 5 overlaps the right side panel 4. To secure the coat 2 in the closed state, an upper hook-and-loop belt 7 is attached to the inside of the left side panel 5, which belt can be attached to a corresponding hook-and-loop element 8 on the right side panel 4 to close the coat 2. Further down, another hook-and-loop belt 9 can be provided on the left side panel 5, which belt interacts with a corresponding hook-and-loop element 10 on the right side panel 4.

The hook-and-loop belts 7, 9 can comprise radiation protection material.

The support skeleton 3 comprises a shoulder/back framework structure 15 that runs in a bow-shape over the shoulders of the person being protected, but is not in direct contact with the shoulders after the radiation protection clothing arrangement has been put on in a ready-to-use state.

To achieve this, the support device 11 is embodied to be height-adjustable. The X-ray protection clothing arrangement 1 can thus be adapted to the body size of the person being protected.

For the height adjustment, an actuation device 13 is for example provided in the form of a push button, which actuation device 13 releases a lock. In order to set the "correct" height, the person being protected stands on his/her tiptoes to raise the X-ray protection clothing arrangement 1. The lock is released with the aid of the actuation device 13, and the support device 11 moves downwards through the effect of gravity until the support caster 12 is resting on the floor. In this state, the support device 11 is locked again. When the person being protected then once again stands on the floor with the soles of his/her feet, a small distance results between the shoulder/back framework structure 15 and the shoulders of the person being protected, and no more weight bears down on the person being protected.

The actuation device 13 is, for example, guided through an opening 14 in the lower hook-and-loop element 10 and thus also enables a radiation protection in the region of the actuation device 13.

Additional details about the support skeleton 3 follow from FIGS. 2A-2E.

As previously mentioned above, the coat 2 is attached to the outside of the support skeleton 3 in the present case, wherein the support skeleton 3 absorbs the weight of the coat 2. The external attachment of the coat 2 to the support skeleton 3 results in a visual, haptic and functional unit.

It should be noted at this juncture that the support skeleton 3 can also be provided externally on the coat 2. However, the support skeleton 3 is preferably integrated into the coat 2, that is, it forms a unit with the coat 2.

The support skeleton 3 comprises a right upper framework structure 16, a left upper framework structure 17, the aforementioned shoulder/back framework structure 15, a right lower framework structure 18, a left lower framework structure 19, and a rear carrying structure 23. The framework structures 15 through 19 and 23 are connected to one another via hinges 26a,b and 27e-h, for example. Instead of hinges, other articulated connections can also be provided. The connection between the framework structures 15 through 19 and 23 can also be achieved via deformable elements, for example, spring rods or the like.

The X-ray protection clothing arrangement 1 can be put on in a simple manner in that the side panels 4, 5 are folded open. The hinges 26a, 27e,f thus enable the folding-open of the right side panel 4 by a simple hand movement. Correspondingly, the hinges 26b, 27g,h enable an outward folding of the left side panel 5. The flexibility of the X-ray protection clothing arrangement 1 in the back and hip region is facilitated via the flexible coat 2 and the flexible properties of the support skeleton 3 by the interaction of flexible structures in the back and front region. Four hinges 27a-d in the front region and eight hinges 31a-h in the back region, as well as four rods 28a-d that are displaceably mounted against four hinges 30a-d, allow an extensive adaptation of the X-ray protection clothing arrangement 1 to the body size of a person being protected, and also allow a correspondingly suitable movability of the person being protected within the X-ray protection clothing arrangement.

As can be seen in FIG. 3, the flexible structures and the elements that are length-variable as a result of the interaction of the rods 28a-d with the rails 30a-d enable a bending-over motion, that is, a bending of the hips and a bending in the lumbar spine.

The support device 11 is arranged in the region of a center plane of the X-ray protection clothing arrangement 1, that is, between the legs 71 of the person being protected, put more precisely, outside of a travel range of the legs 71. The travel range extends out of the interior space past the bottom edge 70 of the coat 2. Accordingly, the support device 11 does not impede a movement of the legs 71.

In other words, the support device is arranged within an extension of the interior space in the direction of gravity.

This embodiment of the X-ray protection clothing arrangement 1 thus has a minimum space requirement and can also be worn in relatively tight locations, such as at an operating table OP (FIG. 11). Standing on a step stool in the operating room during an operation is also possible with this compact embodiment. A typical foot-to-foot situation, as illustrated in FIG. 11, can be achieved with the X-ray protection clothing arrangement 1 so that multiple persons, each of whom is wearing an X-ray protection clothing arrangement 1, can work together at an operating table OP.

As described above, the skeleton is embodied to be movable, that is, intrinsically deformable. The movability can be achieved in that individual elements are connected to one another in an articulated manner, or in that elements themselves are deformable. If an intrinsically deformable support skeleton is used, then the support device can also be arranged outside the extension of the interior space in the direction of gravity, even though the arrangement of the support device within an extension of the interior space in the direction of gravity is advantageous in this case as well.

FIG. 2E schematically shows a way in which the height adjustability of the support device 11 can be achieved.

The support device 11 is displaceably mounted in the rear framework structure 23, but can be secured or locked in this location. This is illustrated by way of example in FIG. 2E.

When the person being protected, who is wearing the X-ray protection clothing arrangement 1, actuates the actuation device 13, a hook 36 is released from a locking position, so that the support device 11 can be displaced relative to the framework structure 23. After the actuation device 13 has been let go of, the support device 11 is once again locked relative to the framework structure 23.

The actuation device 13 is arranged on a housing 24, which in this case is illustrated as a round housing 24 for the sake of simpler explanation. In actuality, the shape of the housing 24 plays a minor role. A pull wire 25 is located in the round housing 24, one end of which wire is attached to a wire fastener 39 in the round housing 24. The other end of the pull wire 29 is guided over two sliding rings 38a,b and then exits the housing 24. The actuation device 13 acts on the pull wire between the two sliding rings 38a,b. When the actuation device 13 is actuated, the pull wire 25 is pulled into the round housing 24.

The pull wire 25 passes over redirection devices 40a,b into another housing 30 in the region of the support device 11, which housing 30 in this case is illustrated as a "angular" housing, with the exact shape being unimportant. In the angular housing, the hook 36 can be displaced against the force of a spring 37 when acted on by the pull wire 25. Thus, when the actuation device 13 is actuated, the hook 36 is pulled into the angular housing 30. When the actuation element 13 is let go of, the hook 36 moves back into its initial position again by the force of the spring 37.

In FIG. 13, it can be seen that the support skeleton 3, of which a section 17b is illustrated in FIG. 13, has a local load-bearing capacity that increases downwards in the direction of gravity. For this purpose, the section 17b comprises a perforation that decreases downwards in the direction of gravity. The size and quantity of the holes thus diminishes downwards in the direction of gravity, so that the entire weight of the X-ray protection clothing arrangement 1 is absorbed by the support skeleton 3 in the lower region of the X-ray protection clothing arrangement 1 in order to improve the stability properties of the X-ray protection clothing arrangement.

FIGS. 4A-4D shows a modified embodiment of the X-ray protection clothing arrangement 1 in which the support device 11 is divided into two support rails 11a, 11b, each of which comprises at its lower end in the direction of gravity a support caster 12a, 12b. The support casters 12a, 12b are preferably embodied as swivel casters and connecting elements 35a, 35b are respectively attached to the rails 11a, 11b. However, the embodiment is selected such that the support device 11 with the rails 11a, 11b does not protrude past the coat 2 on a plane to which the direction of gravity is perpendicular; in other words, the support device 11a, 11l b is arranged within an extension of the interior space in the direction of gravity. In the present case, the support device with the rails 11a, 11b is not arranged between, but rather outside of the legs 71. A travel range for each of the two legs 71 nevertheless remains clear, so that the travel motion of the legs 71 forwards and backwards while standing is still possible.

FIGS. 5A-5D shows a third embodiment in which the support device 11 comprises three rails 11a, 11b, 11c, to each of which a swivel caster 12a, 12b, 12c is attached via a connecting element 35a, 35b, 35c. Here, too, the support device with the rails 11a, 11b, 11c is arranged completely within an extension of the interior space in the direction of gravity. The swivel casters 12a-12c thus do not protrude past the coat 2 in a direction perpendicular to the direction of gravity.

FIGS. 6A-6D shows a fourth embodiment, in which the support device 11 now comprises four rails 11a-11d, which are respectively provided with swivel casters 12a-12d via connecting elements 35a-35d. Here, too, it is ensured that the support casters 12a-12d do not protrude outwardly past the coat 2, that is, on a plane perpendicular to the direction of gravity.

FIGS. 7A-7E schematically shows a fifth embodiment of the X-ray protection clothing arrangement 1, which differs from the embodiment according to FIGS. 1 through 6 in that the support device comprises an exoskeleton 22 for the lower extremities. The exoskeleton 22 comprises an open rear hip ring 43 that is flexibly attached to the right front hip ring 41 and to the left front hip ring 42 via two hinges 63a, 63b. The rear hip ring 43 is furthermore in articulated connection to a right thigh bar 44 and a left thigh bar 45 via a right ball joint 50a and a left ball joint 50b. The two thigh bars 44 and 45 are in turn connected to a right shin bar 46 and a left shin bar 47 via ball joints 50b, 50e. The shin bars 46, 47 are attached to foot bars 48a, 48b via ball joints 50c, 50f. One open ring 49a, 49b each is attached to the shin bars 46, 47, via which rings the exoskeleton 22 is secured to the lower leg of the person being protected. Through a movement of the legs of the person being protected, that is, the upper and lower legs, the exoskeleton 22 is automatically carried along by the open rings 49a, 49b. The foot bars 48a, 48b are respectively attached to a base part 51a, 51b. Additionally, one inner oblong plate 52a, 52b and one outer oblong plate 53a, 53b each can be attached to the base parts 51a, 51b, as well as a rear plate 54a, 54b and a curved plate 55a, 55b. Via the exoskeleton 22, which is part of the support skeleton 3, the weight of the coat 2 is completely transferred onto the floor. The person being protected can place his/her feet on the base parts 51a, 51b through the open rings 49a, 49b. By way of the open rings 49a, 49b and the plates 52a, 52b, 53a, 53b, 54a, 54b and 55a, 55b, the exoskeleton 22 is secured to the lower extremities of the person being protected and is automatically carried along during a movement of the legs. By way of the ball joints 50a-50f and the securing of the exoskeleton 22 to the lower extremities, the exoskeleton 22 enables the free mobility of the hip, knee and ankle joints, e.g., during a walking motion. The person being protected can thus physiologically move with the X-ray protection clothing arrangement 1 without being able to bump into load-bearing supporting structures resting on the ground or being able to perceive said structures as a hindrance.

The term "exoskeleton" 22 does not necessarily mean that the exoskeleton is actually arranged externally on the coat 2. It can also be integrated into the coat 2.

FIG. 7E shows in an exemplary embodiment a ball joint 50 which comprises a ball head 58 that projects into a ball socket of a joint housing 60. Between the ball head 58 and the joint housing 60, a bushing 59 made of an elastic plastic can be provided. On the side opposite of the ball head 58, a rod head 61 projects into a hollow space of the joint housing 60.

Figure 9:
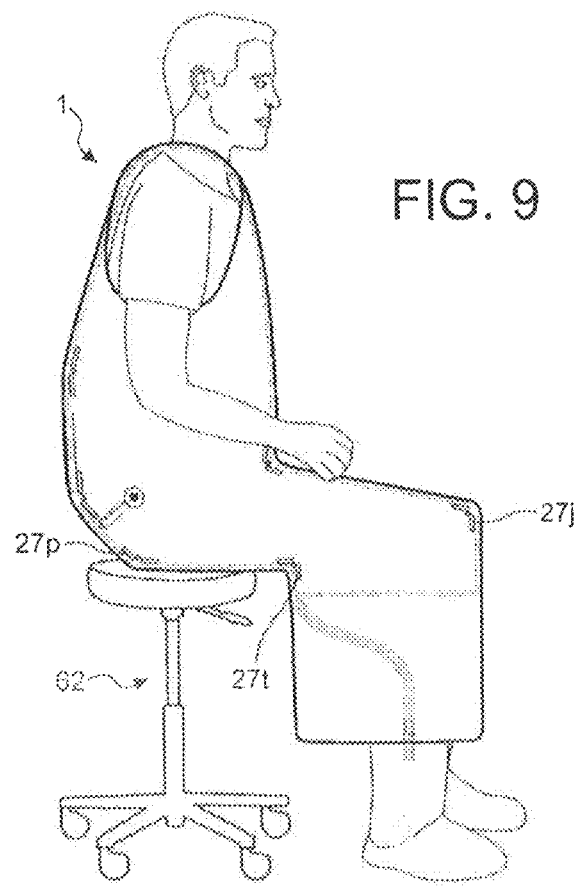
FIG. 9 shows the radiation protection clothing arrangement according to FIG. 8 on a seated person.

In FIGS. 8A-8D, a sixth embodiment of the X-ray protection clothing arrangement 1 is illustrated in which additional flexible elements 27e-27v are provided which ensure added flexibility in the hip and knee region in order to enable sitting, for example, on an operating room stool 62, such as the one illustrated in FIG. 9.

FIGS. 10A-10D shows a seventh embodiment of an X-ray protection clothing arrangement 1 in which, for the sake of simplicity, the support skeleton 3 is only provided in the back region. The comfort and creasing resistance of the coat 2 are somewhat reduced in the front region, but fewer parts are required for production.

FIGS. 1A-1C, 2A-2E, 8A-8D, 9 and 10A-10D show that the support device 11 is connected to the remaining framework structure 23 via a segment 23a of the framework structure designed in an S shape. It is thus possible to position the support caster 12 below a center of mass of the X-ray protection clothing arrangement 1 on a plane perpendicular to the direction of gravity. It is thereby advantageous if the coat 2 and/or the support skeleton 3 have a balanced mass distribution around the support device. Ideally, there is then no tilting moment of the X-ray protection clothing arrangement 1. In reality, however, a slight tilting moment will occur during the use of the X-ray protection clothing arrangement by the person being protected, which moment can, however, be absorbed by the person being protected without any major strain.

Particularly in connection with the bending capability that is illustrated in FIG. 3, it can be advantageous if at least one reset is provided between elements of the support skeleton 3, for example a spring, which make it easier for the person being protected to return to an upright position again from the hunched position. For the sake of clarity, the at least one reset is not illustrated.

In the region of the length-variable elements 28a-28d, 30a-30d, the coat 2 can have an excess length which smooths itself out when the person being protected bends over (FIG. 3).

It is noted that the foregoing examples have been provided merely for the purpose of explanation and are in no way to be construed as limiting of the present invention. While the present invention has been described with reference to an exemplary embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed:

1. A radiation protection clothing arrangement comprising:
   a flexible coat comprising radiation protection material configurable to surround, in a state of use, an interior space and a bottom edge;
   a weight-relieving device that is embodied as a support skeleton connected to the flexible coat at multiple attachment points that are distributed in a direction of gravity so that the support skeleton absorbs a weight of the flexible coat in the multiple locations distributed in the direction of gravity; and a support device, to which the support skeleton is connected, being arranged within a space extending in the direction of gravity from the interior space and being supportable, in the state of use, on an underlying surface, wherein the support device does not protrude outwardly past the flexible coat.

2. The radiation protection clothing arrangement according to claim 1, wherein the support skeleton is embodied to be movable.

3. The radiation protection clothing arrangement according to one of claim 1, wherein the support device comprises at least one caster.

4. The radiation protection clothing arrangement according to claim 1, wherein the support device comprises at least one of a foot attachment or a leg attachment.

5. The radiation protection clothing arrangement according to claim 1, wherein at least one of the coat or the support skeleton has a balanced mass distribution around the support device.

6. The radiation protection clothing arrangement according to claim 1, wherein the support device is arranged outside of leg travel spaces that extend out of the interior space past the bottom edge.

7. The radiation protection clothing arrangement according to claim 1, wherein the support device is height-adjustable.

8. The radiation protection clothing arrangement according to claim 1, wherein the support skeleton is at least partially covered with a textile material.

9. The radiation protection clothing arrangement according to claim 1, wherein the support skeleton is integrated into the coat.

10. The radiation protection clothing arrangement according to claim 1, wherein at least some elements of the support skeleton are embodied to be at least one of length-variable or deformable.

11. The radiation protection clothing arrangement according to claim 10, wherein the coat comprises an excess length in a region of at least one of the length-variable or deformable elements.

12. The radiation protection clothing arrangement according to claim 1, wherein the support skeleton is formed from at least one of metal or plastic.

13. The radiation protection clothing arrangement according to claim 1, wherein the support skeleton comprises at least one of a framework structure or a perforated plate arrangement.

14. The radiation protection clothing arrangement according to claim 1, wherein the support skeleton has a local load-bearing capacity that increases downwards in the direction of gravity.

15. The radiation protection clothing arrangement according to claim 1, wherein at least one movable connection between elements of the support skeleton comprises at least one reset.

16. The radiation protection clothing arrangement according to claim 1, wherein the support device is arranged entirely within the space extending from the interior space in the direction of gravity.

17. The radiation protection clothing arrangement according to claim 1, wherein the support device is arranged to extend, in the direction of gravity, from the interior space into a space extending, in the direction of gravity, below the bottom edge.

18. A method of wearing the radiation protection clothing arrangement according to claim 1, comprising:

placing a part of the support skeleton over a wearer's shoulders;

closing the flexible coat to surround at least the wearer's torso to define the interior space; and adjusting a length of the support device so that the support device is supported on the underlying surface, to which the support skeleton is connected, wherein, after adjusting the length of the support device, the wearer's shoulders do not bear a weight of the support skeleton.

19. The method according to claim 18, wherein, while adjusting the length of the support device, the support device remains within the space extending from the interior space in the direction of gravity.

20. The method according to claim 18, wherein the support device includes an actuation device that is configured to release the support device from a locked position and to lock the support device in a support position.

* * * * *